(12) United States Patent
Sandal et al.

(10) Patent No.: US 7,608,288 B2
(45) Date of Patent: Oct. 27, 2009

(54) **CAFFEINE FRACTION OBTAINED FROM TEA LEAVES AND A METHOD FOR INDUCING *AGROBACTERIUM TUMEFACIENS*-MEDIATED GENETIC TRANSFORMATION IN PLANTS USING SAID CAFFEINE FRACTION**

(75) Inventors: Indra Sandal, Himachal Pradesh (IN); Ajay Kumar, Himachal Pradesh (IN); Amita Bhattacharya, Himachal Pradesh (IN); Ravindranath Srigiripuram Desikalhar, Himachal Pradesh (IN); Ashu Gulati, Himachal Pradesh (IN); Paramvir Singh Ahuja, Himachal Pradesh (IN)

(73) Assignee: Council of Scientific & Industrial Research, New Delhi (IN)

( * ) Notice: Subject to any disclaimer, the term of this patent is extended or adjusted under 35 U.S.C. 154(b) by 334 days.

(21) Appl. No.: 10/396,593

(22) Filed: Mar. 25, 2003

(65) Prior Publication Data

US 2004/0009544 A1    Jan. 15, 2004

(51) Int. Cl.
*A61K 36/82* (2006.01)
*C07D 473/00* (2006.01)
(52) U.S. Cl. ........................ 424/729; 544/274
(58) Field of Classification Search ............. None
See application file for complete search history.

(56) References Cited

FOREIGN PATENT DOCUMENTS

JP            02184626 A  *  7/1990

OTHER PUBLICATIONS

Wörth, C. C. T.; Wießier, M.; Schmitz, O. J. Electrophoresis. 2000, 21, 3634-3638.*
Chen, Z.-Y.; Zhu, Q. Y.; Tsang, D.; Huang, Y. J. Agric. Food Chem. 2001, 49(1), 477-482.*
http://web.archive.org/web/*/http://www.newton.dep.anl.gov/askasci/chem00/chem00291.htm (Web Publication Date: Apr 23, 2001). Date Accessed: Dec. 13, 2006.*
By http://en.wikipedia.org/wiki/Chloroform.*
Wörth, C. C. T.; Wießier, M.; Schmitz, O. J. Electrophoresis. 2000, 21, 3634-3638.*
Chen, Z.-Y.; Zhu, Q. Y.; Tsang, D.; Huang, Y. J. Agric. Food Chem. 2001, 49(1), 477-482.*
Mondal, T.K.; Bhattacharya, A.; Ahuja, P.S. and Chand, P.K. 'Transgenic tea [*Camellia sinensis* (L.) O. Kuntze cv. Kangra Jat] plants obtained by Agrobacterium-mediated transformation of somatic embryos'. Plant Cell Rep, No. 20 (2001) pp. 712-720.*
Steinkraus, K.H.; Shapiro, K.B.; Hotchkiss, K.B. and Mortlock, R.P. 'Investigations into the Antibiotic Activity of Tea Fungus/Kombucha Beverage'. Acta Biotechnol. vol. 16, No. 2-3 (1996) pp. 199-205.*
http://web.archive.org/web/*/http://www.newton.dep.anl.gov/askasci/chem00/chem00291.htm (Web Publication Date: Apr. 23, 2001). Date Accessed: Dec. 13, 2006.*
http://en.wikipedia.org/wiki/Chloroform.*

* cited by examiner

*Primary Examiner*—Christopher R Tate
*Assistant Examiner*—Amy L Clark
(74) *Attorney, Agent, or Firm*—Arent Fox LLP

(57) ABSTRACT

The present invention relates to a thermolabile caffeine fraction useful for an efficient *Agrobacterium*-mediated genetic transformation in plant systems to develop desired traits in plants, and a method of preparing said fraction from tea leaves and also, an efficient and cost-effective method of introducing said *Agrobacterium*-mediated genetic transformation into plant systems using said caffeine fraction of tea leaves.

2 Claims, 4 Drawing Sheets

Figure 1:
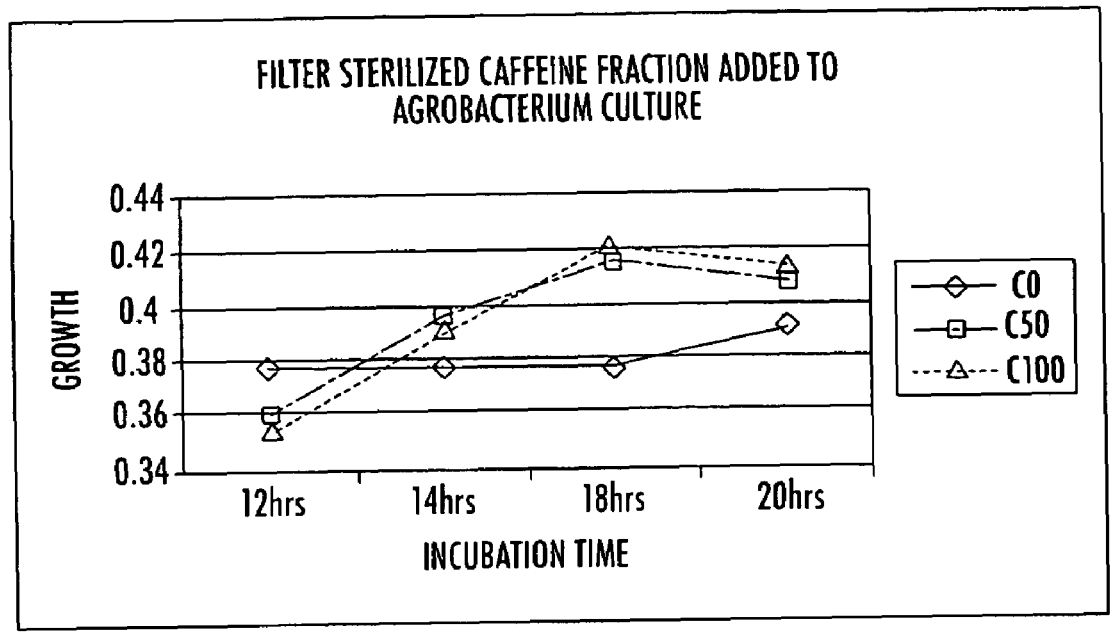
Figure 1:
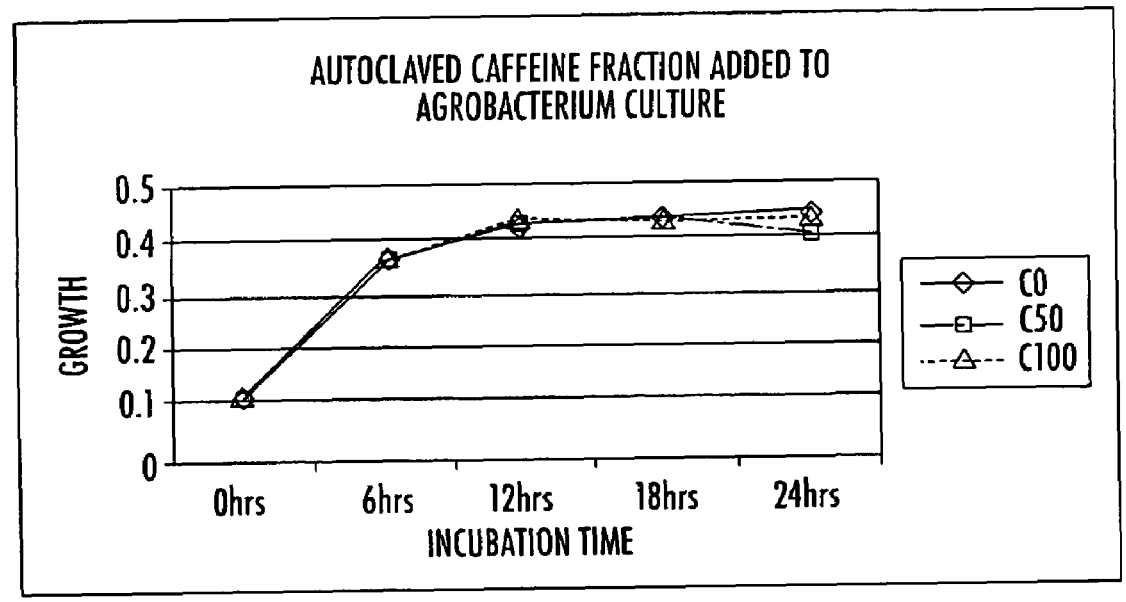

CAFFEINE FRACTION OBTAINED FROM TEA LEAVES AND A METHOD FOR INDUCING *AGROBACTERIUM TUMEFACIENS*-MEDIATED GENETIC TRANSFORMATION IN PLANTS USING SAID CAFFEINE FRACTION

FIELD OF THE PRESENT INVENTION

The present invention relates to a thermolabile caffeine fraction useful for an efficient *Agrobacterium*-mediated genetic transformation in plant systems to develop desired traits in plants, and a method of preparing said fraction from tea leaves and also, an efficient and cost-effective method of introducing said *Agrobacterium*-mediated genetic transformation into plant systems using said caffeine fraction of tea leaves.

BACKGROUND AND PRIOR ART REFERENCES OF PRESENT INVENTION

*Agrobacterium* is a gram negative soil bacterium that transfers its Ti plasmid or the 'Tumor inducing plasmid' into the cells of most dicotyledonous plants and quite a good number of monocotyledonous plants. The Ti plasmid undergoes cell-cell recognition, signal transduction, cellular and nuclear import and finally T-DNA integration (Winans S C Two-way chemical signaling in *Agrobacterium*-plant interactions Microbiological-Reviews. 1992, 56: 1, 12-31).

The transfer DNA or the T-DNA harboring the oncogenes bounded by the 25 bp imperfect border repeats on either side brings about genetic transformation and hence crown gall disease. The process of signal transduction is initiated by a set of several 'virulence genes', of which 7 genes are the most important.

The first step of signal reception and then transduction is triggered by the inducers like phenolics and sugars (Ankenbauer R G; Nester E W Sugar-mediated induction of *Agrobacterium tumefaciens* virulence genes: structural specificity and activities of monosaccharides. Journal of Bacteriology. 1990, 172: 11, 6442-6446).

For the past two decades, revolutionary work has been done on development of genetically transformed plants wherein, the disarmed strains of *Agrobacterium* (i.e. the Ti plasmid with the oncogenes replaced by genes of interest) are employed to produce plants as per ones requirements at a much shorter time. The inducers that are used for such genetic transformation experiments are generally the Acetosyringone (Morris J W; Morris R O Identification of an *Agrobacterium tumefaciens* virulence gene inducer from the Pinaceous gymnosperm *Pseudotsuga menziesii*. Proceedings of the National Academy of Sciences of the United States of America 1990, 87: 9, 3614-3618) and the Hydroxy-acetosyringone that are commercially provided by the Sigma Aldrich Company, USA.

Tea leaves when extracted, are known to have fractions of caffeine, catechins and other flavonols and amino acids. Some chance experiments indicated that particular fractions of tea containing caffeine are capable of promoting infection by *Agrobacterium*, cell-cell recognition and virulence. This led us to believe that the caffeine fractions can be used as a virulence inducer during genetic transformation experiments instead of Acetosyringone or Hydroxy-acetosyringone.

Besides containing high levels of the 6 types of catechins (C) and their derivatives viz., epicatechin (EC), gallocatechins (GC), epigallocatechins (EGC), epicatechin gallate (ECg), epigallocatechin gallate (EGCg), tea leaves also contain caffeine, amino acids, nitrogenous compounds, vitamins, inorganic elements, carbohydrates and lipids (Chu D C and Juneja L. R. General chemical composition of green tea and its infusion. In: Chemistry and Application of Green Tea. 1997. CRC Press, N. York. eds. Yamamoto T., Juneja L. R., Chu D C, Kim M., pp.).

The report of Sunilkumar et al., 1999. (Sunilkumar G; Vijayachandra K; Veluthambi K 1999, Pre-incubation of cut tobacco leaf explants promotes *Agrobacterium*-mediated transformation by increasing vir gene induction. Plant Science Limerick. 141: 1, 51-58) indicated that the requirement of preincubation for increased transformation efficiency can be obviated by the addition of 100 µM acetosyringone to the freshly cut leaf rings during the co-cultivation with *Agrobacterium*. The production of vir gene inducers by the leaf rings during the pre-incubation period is an important factor that contributes to increased transformation efficiency of *Agrobacterium* upon pre-incubation but the drawback is that the effect of the inducer 'acetosyringone' and pre-incubation is similar and thus inducers do not have much role to play.

Expression of *Agrobacterium tumefaciens* virulence (vir) genes and transformation of dicots by this organism are dependent upon host plant phenolic compounds and several alkylsyringamides, syringic acid, synthetic amides like ethylsyringamide, ferulic or sinapic acids are powerful inducers of vir genes (Vir gene inducing activities of hydroxycinnamic acid amides in *Agrobacterium tumefaciens* Berthelot, K; Buret, D; Guerin, B; Delay, D; Negrel, J; Delmotte, F M. Phytochemistry. 1998, 49: 6, 1537-1548).

However, none of the inducers tested exhibited higher activity than acetosyringone, the reference compound for vir gene induction, with the exception to ethylsyringamide at concentrations above 1 mM. When tested on *A. tumefaciens* strain A348 (pSM243cd), ethylferulamide and ethylsinapamide are more efficient than the corresponding phenolic acids but only above 100 µM.

The major draw back is that the above mentioned inducers are very expensive chemical compounds that are required to be used at high concentrations above 100 µM. Moreover, the compounds like acetosyringone are manufactured only by a few select companies like Sigma Aldrich and requires import from United States of America by research laboratories situated in developing countries.

Lee et al., 1995 (Lee, YongWoog; Jin, ShouGuang; Sim, WoongSeop; Nester, E W; Lee, Y W; Jin, S G; Sim, W S Proceedings of the National Academy of Sciences of the United States of America. 1995 Genetic evidence for direct sensing of phenolic compounds by the VirA protein of *Agrobacterium tumefaciens*. 92: 26, 12245-12249.) reported that the virulence (vir) genes of *Agrobacterium tumefaciens* are induced by low-molecular-weight phenolic compounds and monosaccharides through a two-component regulatory system consisting of the VirA and VirG proteins. The vir-inducing abilities of 15 different phenolic compounds like acetovanillone was tested using four wild-type strains of *A. tumefaciens* KU12, C58, A6, and Bo542. By transferring different Ti plasmids into isogenic chromosomal backgrounds, the phenolic-sensing determinant was shown to be associated with Ti plasmid. Subcloning of Ti plasmid indicates that the vira locus determines which phenolic compounds can function as vir gene inducers. These results suggest that the VirA protein directly senses the phenolic compounds for vir gene activation. The drawback of this report is that subcloning of Ti plasmid is required for the identification of the accurate phenolics inducer for vir a locus.

Hess et al., 1991 (Hess, K M; Dudley, M W; Lynn, D G; Joerger, R D; Binns, A N. 1991, Mechanism of phenolic activation of *Agrobacterium* virulence genes: development of a specific inhibitor of bacterial sensor/response systems. Proceedings of the National Academy of Sciences of the United States of America. 1991, 88: 17, 7854-7858) reported that the aglycone of the dihydrodiconiferyl alcohol glycosides were potent inducers of virulence gene expression in *A. tumefaciens*. Using this model, a specific inhibitor of vir induction was developed. The drawback of this report is that this inhibitor did not affect the induction of other genes on the Ti plasmid but irreversibly blocks vir expression.

Fortin et al., 1992 (Fortin, C; Nester, E W; Dion, P. 1992, Growth inhibition and loss of virulence in cultures of *Agrobacterium tumefaciens* treated with acetosyringone. Journal of Bacteriology. 174: 17, 5676-5685) reported that acetosyringone, a phenolic inducer of the virulence (vir) genes of *A. tumefaciens*, inhibited the growth of the nopaline type strains T37 and C58 incubated under acidic conditions. Two other vir inducers, sinapinic acid and syringaldehyde, also inhibited growth and promoted accumulation of avirulent clones in cultures of strains C58F and T37. On the other hand, various acetosyringone analogues reported not to induce the vir genes did not act as growth inhibitors. Mutants of strain C58F lacked the capacity to induce a virB::lacZ fusion in the presence of acetosyringone. The drawback of this report is that while some inducers were promotive, others are inhibitory and are also strain specific.

Delmotte et al., 1991 (Delmotte F M; Delay D; Cizeau J; Guerin B; Leple J C 1991. *Agrobacterium* vir-inducing activities of glycosylated acetosyringone, acetovanillone, syringaldehyde and syringic acid derivatives. Phytochemistry., 30: 11, 3549-3552.) reported that when *A. tumefaciens* str. A348 (pSM358) harboring a virE::lacZ fusion plasmid was used to detect the ability of 13 synthetic acetosyringone, acetovanillone, syringaldehyde and syringic acid beta-glycosides to induce virulence, the activity of the reporter beta-galactosidase was detected by spectrofluorimetry using 4-methylumbelliferyl beta-galactopyranoside as substrate. Acetosyringonyl beta-L-fucopyranoside was the most active monoglycoside tested; even at high concentrations this compound was devoid of toxic effects. However, monoglycosides were less active vir inducers than free acetosyringone. In contrast, the beta-maltoside of syringaldehyde showed higher activity than the free phenol at high concentrations. The activity of such glycosylated inducers may be related to specific sugar receptors on the bacterial cell surface. The drawback of the report is that the acetosyringone is costly compound that need to be imported from Sigma Aldrich, USA.

OBJECTS OF THE PRESENT INVENTION

The main object of the present invention is to develop a thermolabile caffeine fraction useful for *Agrobacterium*-mediated genetic transformation in plants.

Yet another object of the present invention is to characterize the thermolabile caffeine fraction obtained from tea leaves.

Still another object of the present invention is to develop a fraction from tea leaves with an ability to induce strain non-specific *Agrobacterium*-mediated genetic transformation in plants.

Still another object of the present invention is to develop a natural and effective inducer for *Agrobacterium*-mediated genetic transformation in plants.

Still another object of the present invention is to develop an economical and cost-effective inducer for *Agrobacterium*-mediated genetic transformation in plants.

Still another object of the present invention is to determine the ideal concentration range of the chloroform fraction of tea leaf for *Agrobacterium*-mediated genetic transformation in plants.

Further, another object of the present invention is to develop a method of preparing a thermolabile caffeine fraction from tea leaves.

Another main object of the present invention is to develop a method to method of preparing chloroform fraction from the tea leaf extract having the property of inducing *Agrobacterium*-mediated genetic transformation in plants.

Further, another object of the present invention is to develop an efficient method for introducing said *Agrobacterium*-mediated genetic transformation into plants.

Another object of the present invention is to develop an efficient method for introducing said *Agrobacterium*-mediated genetic transformation into plants using said caffeine fraction of tea leaves.

Yet another object of the present invention is to develop a cost-effective method of introducing said *Agrobacterium*-mediated genetic transformation into plants.

Still another object of the present invention is to develop a method for introducing said *Agrobacterium*-mediated genetic transformation into plants using naturally occurring sources.

Still another object of the present invention is to develop a substitute for the cost of the transformation inducers like acetosyringone and hydroxy-acetosyringone.

Further, another object of the present invention is to develop a method for introducing genes of desired traits in plants by *Agrobacterium*-mediated genetic transformation into plants using said caffeine fraction of tea leaves.

Further, another object of the present invention is to compare the transformation inducing capability of both autoclaved and filter sterilized caffeine fractions.

SUMMARY OF THE PRESENT INVENTION

The present invention relates to a thermolabile caffeine fraction useful for an efficient *Agrobacterium*-mediated genetic transformation in plant systems to develop desired traits in plants, and a method of preparing said fraction from tea leaves and also, an efficient and cost-effective method of introducing said *Agrobacterium*-mediated genetic transformation into plant systems using said caffeine fraction of tea leaves.

DETAILED DESCRIPTION OF THE PRESENT INVENTION

Accordingly, the present invention relates to a thermolabile caffeine fraction useful for an efficient *Agrobacterium*-mediated genetic transformation in plant systems to develop desired traits in plants, and a method of preparing said fraction from tea leaves and also, an efficient and cost-effective method of introducing said *Agrobacterium*-mediated genetic transformation into plant systems using said caffeine fraction of tea leaves.

In an embodiment of the present invention, wherein a cost-effective and efficient method of using thermolabile caffeine fraction of tea leaves as a natural inducer for bacteria *Agrobacterium tumefaciens* mediated genetic transformations in plants to produce desired traits in the plants, said method comprising step of:

inoculating strains of the bacteria into liquid modified Yeast Mannitol Broth, incubating the inoculum for about 12-16 hrs at about 25-30° C., at about 150-200 rpm in dark, harvesting the incubated inoculum at about 0.6-0.8 optical density at 600 nm for $1\times10^9$ cells/ml during log phase of bacterial growth to obtain pellet, suspending the pellet in fresh Yeast Mannitol Broth without damaging the bacterial cells to obtain a suspension, immersing explants of different plants in bacterial suspension for about 5-35 minutes, incubating explants on incubation medium for different periods of 1-10 days, using caffeine fraction at concentrations of about 0.5-300 μg/ml in fresh cultures of the bacteria to induce vir genes, thereby transferring Ti plasmid harboring the transgene into the plant for genetically transforming the plants with genes of desired traits.

In another embodiment of the present invention, wherein pelleting of living bacterial cells by centrifugation at 15-30 minutes at 4000-8000 rpm and 25-30° C.

In yet another embodiment of the present invention, wherein caffeine fraction is better inducer as compared to commercially available inducers.

In still another embodiment of the present invention, wherein a method of preparing thermolabile caffeine fraction from the tea plant, said method comprising steps of:

extracting dried tea leaves overnight at room temperature with about 10-40% aqueous acetone, filtrating tea leaves extract with n-hexane to obtain aqueous and lipid layers, extracting the aqueous layer with petroleum ether and ethyl acetate to remove catechins from the aqueous layer, extracting aqueous layer of step (c) with chloroform to obtain chloroform layer, estimating total caffeine fraction concentration in the chloroform layer, sterilizing caffeine fraction both by autoclaving and filter sterilization to obtain said fraction.

In still another embodiment of the present invention, wherein a thermolabile caffeine fraction.

In another embodiment of the present invention, a thermolabile caffeine fraction of tea leaves—a substitute for acetosyringone for *Agrobacterium* mediated genetic transformations which comprises step of:

(i) inoculation of two strains of *Agrobacterium tumefaciens* viz. EHA105 (mild) and GV2260 (virulent) harboring the antibiotic resistance genes for kanamycin or hygromycin and the reporter gus gene from mother cultures of respective strains into 10-30 ml liquid modified Yeast Mannitol Broth with kanamycin or hygromycin, (ii) incubation for 12-16 hrs at 25-30° C. and 150-200 rpm in dark, (iii) harvesting at 0.6-0.8 optical density at 600 nm for $1\times10^9$ cells/ml during log phase of bacterial growth, (iv) pelleting of living bacterial cells by centrifugation at 15-30 minutes at 4000-8000 rpm and 25-30° C., (v) suspension of bacterial pellet in fresh 5-25 ml of Yeast Mannitol Broth without damaging the bacterial cells, (vi) optimization of bacterial cell density at $1\times10^9$ cells/ml by measuring optical density at 600 nm, (vii) immersion of various explants of different plants in bacterial suspension for 5-35 minutes, (viii) blotting of explants on filter papers to remove excess *Agrobacterium tumefaciens*, (ix) incubation of explants on incubation medium for different periods of 1-10 days, (x) 100-500 g fresh tea leaves of Kangra jat dried in an oven at 60° C. to a constant weight, (xi) dried leaves extracted overnight at room temperature with 0.4-1.2 litres of 10-40% aqueous acetone and filtered, (xii) the filterate extracted with 100-500 ml of n-hexane to obtain two layers for removal of lipids, (xiii) the aqueous layer taken and extracted with petroleum ether (100-300 ml) and ethyl acetate (100-400 ml) to remove catechins, (xiv) aqueous layer taken and extracted with chloroform (100-400 ml) and ammonia solution (3-10%), (xv) chloroform layer concentrated to 10-50 ml and total caffeine estimated, (xvi) concentrated chloroform layer serves as a caffeine fraction, (xvii) sterilization of caffeine fraction both by autoclaving and filter sterilization (xviii) use of caffeine fraction at concentrations of 0.5-300 μg/ml in fresh cultures of *Agrobacterium tumefaciens* instead of acetosyringone.

(xix) transfer of various explants of different plants to regeneration medium containing different concentrations of 0.5-300 μg/ml caffeine fractions for inducing the vir genes and increasing the transformation efficiency.

Figure 2:
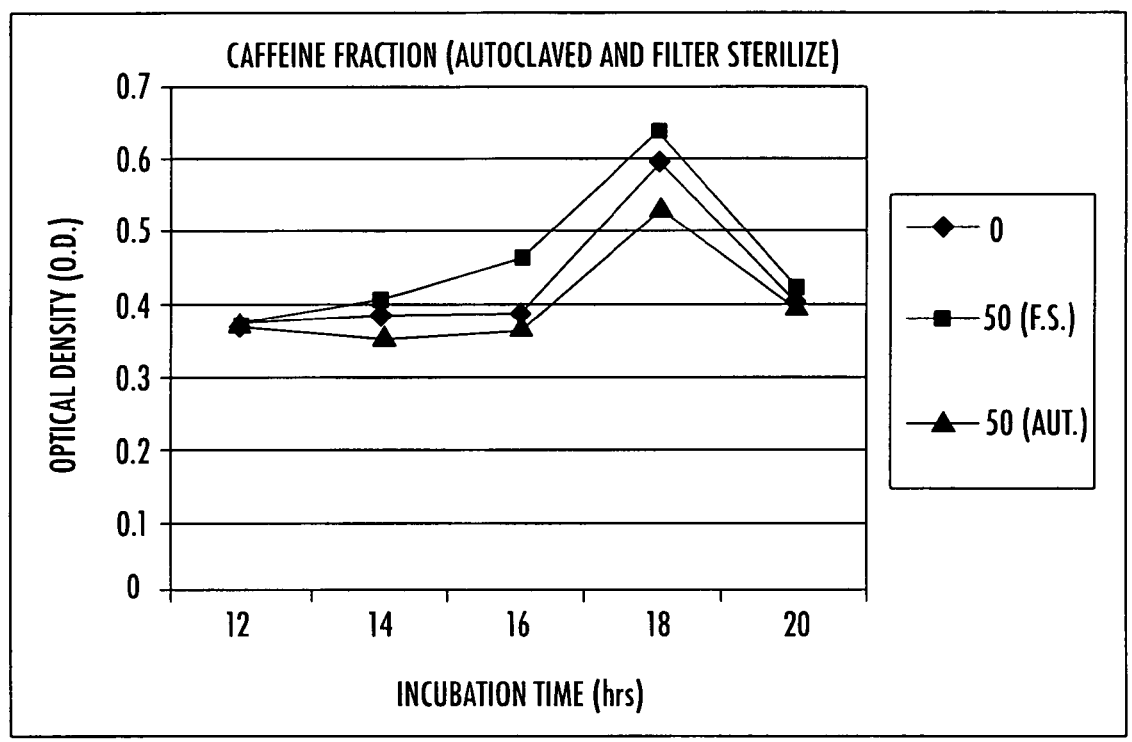

(xx) transfer of *Agrobacterium tumefaciens* free explants to regeneration medium containing selection antibiotics for further regeneration and transgenic plant development, and (xxi) comparative analysis of the caffeine fraction (both autoclave and filter sterilized—please refer FIGS. 1 and 2) and catechin fraction and the crude tea extract though HPLC using acetonitrile and phosphoric acid in gradient mode (0.05 to 0.2%) for detection of virulence inducing compound using diode array detector at 250 to 280 nm wavelength as shown in Table 1 and 2 here below.

TABLE 1 filter sterilized caffeine fraction

| Conc (μg/ml) | 12 hrs | 14 hrs | 18 hrs | 20 hrs |
|---|---|---|---|---|
| C0 | 0.377 | 0.377 | 0.377 | 0.393 |
| C50 | 0.36 | 0.396 | 0.416 | 0.409 |
| C100 | 0.352 | 0.39 | 0.423 | 0.415 |

TABLE 2 autoclaved caffeine fraction

| Conc (μg/ml) | 0 hr | 6 hrs | 12 hrs | 18 hrs | 24 hrs |
|---|---|---|---|---|---|
| C0 | 0.1 | 0.37 | 0.42 | 0.443 | 0.445 |
| C50 | 0.104 | 0.367 | 0.429 | 0.423 | 0.402 |
| C100 | 0.109 | 0.371 | 0.44 | 0.428 | 0.432 |

In still another embodiment of the present invention, genetic transformation in plants via *Agrobacterium* is brought about by induction of virulence or vir genes and transfer of the Ti plasmid harboring the transgene into the plant tissue. Transgenes that code for desirable traits like disease and stress resistance, crop quality, flavors, colors, better shelf life when introduced into the plant tissues can bring about crop improvement in a shorter time than conventional breeding. Generally phenolic inducers are responsible for the induction of the vir genes and the popular commercially available inducers are the acetosyringone or the hydroxy-acetosyringone. These commercially available inducers are not only expensive but are also confined to few select companies like Sigma Aldrich, USA.

In still another embodiment of the present invention, caffeine fraction of tea leaves has the potential for substituting these commercially available inducers as they can induce the vir genes and bring about genetic transformation. This natural fraction that is easily available is not only cost effective but can also improve the transformation efficiency. In another embodiment of the present invention, the virulence inducer caffeine fraction from tea leaves can be used for transgenic production using different explants of different plant species.

In still another embodiment of the present invention, different concentrations of filter sterilized caffeine fractions of tea leaves were added as above.

In still another embodiment of the present invention, different concentrations of autoclaved caffeine fractions of tea leaves were added as above.

Figure 3:
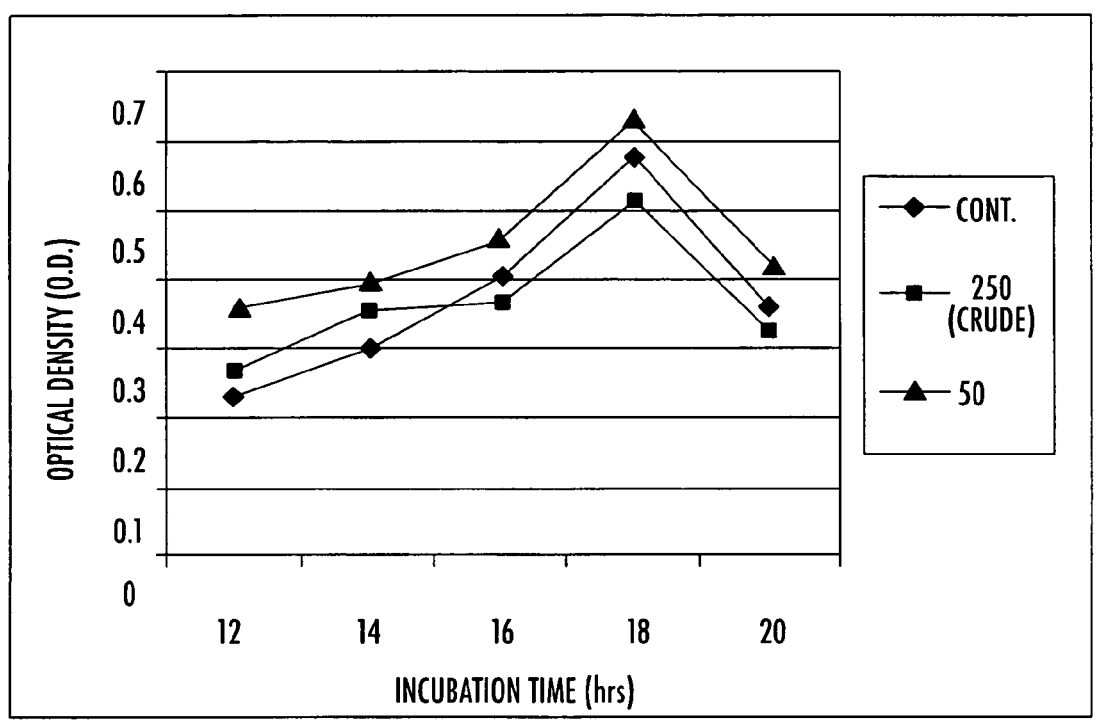

In still another embodiment of the present invention, *Clostridium perfringens*, a foodborne pathogen, exerts its toxic effect on humans when producing a toxin during sporulation in the intestine. Investigations were undertaken to determine the effect of caffeine which is consumed in large amounts worldwide in the diet on sporulation and subsequent toxin formation. In the presence of 100 μg caffeine/ml or 200 μg theobromine/ml, sporulation of *C. perfringens* NCTC 8679 rose from <1 to 80 or 85%. Enterotoxin concentration increased from undetectable levels to 450 μg/mg of cell extract protein. Heat-resistant spore levels increased from <1000 to between 1×107 and 2×107/ml. Caffeine caused a 3- to 4-fold increase in the percentages of cells possessing retractile spores and a similar increase in enterotoxin concentration.

In still another embodiment of the present invention, the study on mechanism by which caffeine stimulates sporulation of *C. perfringens* indicated that cultures exposed to caffeine had significantly elevated levels of intracellular adenosine and guanosine triphosphates (Nolan L L; Labbe R G; Craker L E (ed.); Nolan L (ed.); Shetty K Effect of plant alkaloids on the sporulation of a food-borne pathogen. International symposium on medicinal and aromatic plants, Amherst, Mass., USA, Aug. 27-30, 1995. Acta-Horticulturae. 1996, No. 426, 287-295). This property led us to employ the caffeine fraction from tea leaves for inducing of virulence genes in *Agrobacterium* mediated genetic transformations and also a substitute of an expensive chemical acetosyringone. Moreover, since the the virulence inducer caffeine fraction from tea leaves are also obtained from the maintenance foliage leaves that are generally discarded and burnt, this method appears to be all the more economical and cost effective. Use of the virulence inducer caffeine fraction from tea leaves is specially important in increasing the transformation efficiency.

In still another embodiment of the present invention, a thermolabile caffeine fraction of tea leaves—a substitute of acetosyringone for *Agrobacterium* mediated genetic transformations. (see FIG. 4)

In still another embodiment of the present invention, a thermolabile caffeine fraction of tea leaves—a substitute for acetosyringone for *Agrobacterium* mediated genetic transformations obviates the drawbacks as detailed above.

In still another embodiment of the present invention, the novelty of this method is that a cost effective natural extract was identified that could substitute for the cost of the inducers like acetosyringone and hydroxy-acetosyringone.

In still another embodiment of the present invention, the caffeine fraction of tea leaves can be used for *Agrobacterium tumefaciens* mediated genetic transformation of different systems or plants or explants.

In still another embodiment of the present invention, an economical system for obtaining an inducer without involving any costly extraction methods wherein the crude leaf extract with bactericidal activity is also extracted without requiring expensive instruments.

In still another embodiment of the present invention, the caffeine fraction of tea leaf with virulence inducer activity can be obtained in abundance from naturally growing tea bushes.

In still another embodiment of the present invention, the virulence inducer caffeine fraction from tea leaves is of natural origin and is not of synthetic or semi-synthetic nature.

In still another embodiment of the present invention, the virulence inducer caffeine fraction from tea leaves can be obtained in abundance from actively growing apical shoots i.e. two and a bud making it economical.

In still another embodiment of the present invention, the virulence inducer caffeine fraction from tea leaves can be obtained in abundance even from the lower maintenance foliage thereby making it more economical as generally such leaves are discarded or burnt.

In still another embodiment of the present invention, the crude extract can also be used during 'hairy root production' using *Agrobacterium rhizogenesis.*

In still another embodiment of the present invention, the transformation efficiency by *Agrobacterium* can be increased considerably.

In still another embodiment of the present invention, use of tea leaf extract for *Agrobacterium tumefaciens* genetic transformation in different systems or plants or explants wherein the generally used synthetic inducers are ineffective.

In still another embodiment of the present invention, deriving a cost effective system for *Agrobacterium tumefaciens* genetic transformation wherein no commercial and yet costly inducers are used.

The crude tea leaf extract in patent no NF 14/02 was obtained by using acetone and n-hexane where as the caffeine fraction in patent no NF 221/02 was obtained by using solvent extraction using ethyl acetate and petroleum benzene for removal of catechins. The crude tea leaf extract contained generally catechin and caffeine whereas the caffeine fraction had only caffeine, therefore they should not be treated as one. The supporting data in FIG. 3 represents: Effect of different fractions of tea extract on the growth of *Agrobacterium tumefaciens* culture. This clearly substantiates the difference between both the fractions.

Use of caffeine fraction at concentrations of 0.5-300 μg/ml in the medium of fresh cultures of *Agrobacterium tumefaciens* instead of acetosyringone. This refers to the concentration of caffeine in the culture medium and actually refers to concentrations ranging from 0.5-300 μg of caffeine in the medium. The concentration of the inducer is indirectly estimated as the concentration of caffeine in the fraction.

BRIEF DESCRIPTION OF THE ACCOMPANYING DRAWING

FIG. 1 shows effect of filter sterilized and autoclaved caffeine tea fraction on the growth of *Agrobacterium tumefaciens* culture.

FIG. 2 shows comparison of filter sterilized and autoclaved caffeine fractions.

FIG. 3 shows effect of different fractions of tea extract on the growth of *Agrobacterium tumefaciens* culture.

Figure 4:
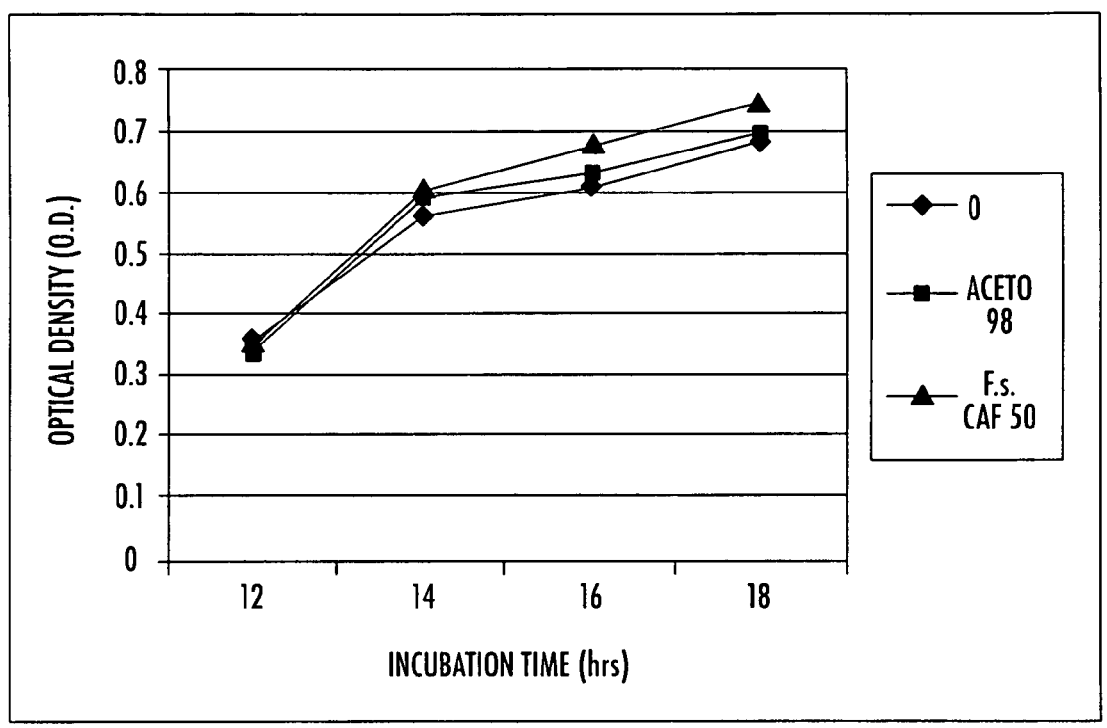

FIG. 4 shows comparison of the effect of acetosyringone and the caffeine fraction on the growth of *Agrobacterium tumefaciens*.

The following examples are given by way of illustration and therefore should not be construed to limit the scope of the present invention.

EXAMPLE 1

Two strains of *Agrobacterium tumefaciens* viz. EHA105 (mild) and GV2260 (virulent) harboring the antibiotic resistance genes for kanamycin or hygromycin and the reporter gus gene from mother cultures of respective strains were inoculated into 10-30 ml liquid modified Yeast Mannitol Broth with kanamycin or hygromycin and incubated for 12-16 hrs at 25-30° C. and 150-200 rpm in dark. Cells were harvested at 0.6-0.8 optical density at 600 nm for $1\times10^9$ cells/ml during log phase of bacterial growth.

Living bacterial cells were pelleted of by centrifugation at 15-30 minutes at 4000-8000 rpm and 25-30° C. Bacterial pellet was suspended in fresh 5-25 ml of Yeast Mannitol Broth without damaging the bacterial cells and cell density was optimized at $1\times10^9$ cells/ml by measuring optical density at 600 nm. Various explants of different plants were immersed in bacterial suspension for 5-35 minutes. Explants were blotted on filter papers to remove excess *Agrobacterium tumefaciensis*. Explants incubated on incubation medium for different periods of 1-10 days. Fresh tea leaves (100-500 g) of Kangra jat dried in an oven at 60° C. to a constant weight and extracted overnight at room temperature with 0.4-1.2 litres of 10-40% aqueous acetone and filtered. The filtrate extracted with 100-500 ml of n-hexane to obtain two layers for removing lipids. The aqueous layer was extracted with petroleum ether (100-300 ml) and ethyl acetate (100-400 ml) to remove catechins. The aqueous layer was taken and extracted with chloroform (100-400 ml) and ammonia solution (3-10%). The chloroform layer was concentrated to 10-50 ml and total caffeine was estimated. The concentrated chloroform layer served as a caffeine fraction and was sterilized both by autoclaving and filter sterilization method. The concentrated chloroform layer served as a caffeine fraction which was used at concentrations of 0.5-300 µg/ml in fresh cultures of *Agrobacterium tumefaciens*. Various explants of different plants were transferred to regeneration medium containing different concentrations of 0.5-300 µg/ml caffeine fractions for inducing the vir genes and increasing the transformation efficiency. *Agrobacterium tumefaciens* free explants were transferred to regeneration medium containing selection antibiotics for further regeneration and transgenic plant development. Comparative analysis of the three fractions viz. the caffeine fraction (both autoclave and filter sterilized), the catechin fraction and the crude tea extract though HPLC. Acetonitrile and phosphoric acid (0.05 to 0.2%) were used in gradient mode for detection of 'virulence inducing compound' with the help of diode array detector at 250 to 280 nm wavelength.

EXAMPLE 2

Caffeine fractions were filter sterilized and used as an inducing agent instead of acetosyringone in different explants for *Agrobacterium tumefaciens* mediated transformations as described above in Example-1.

EXAMPLE 3

Caffeine fractions were autoclaved used as an inducing agent instead of acetosyringone in different explants for *Agrobacterium tumefaciens* mediated transformations as described above in Example-1 and 2.

The main advantages of the present invention are:

(1) Caffeine fraction of tea leaf can be used as a potent virulence inducing agent for *Agrobacterium tumefaciens* mediated genetic transformations instead of acetosyringone.
(2) Caffeine fraction of tea leaf can be used for *Agrobacterium tumefaciens* mediated genetic transformation in different systems or plants or explants wherein the commercially used virulence inducing agent acetosyringone is ineffective.
(3) Since no commercial virulence inducer need to be used, caffeine fraction of tea leaf prove to be a cost effective system for *Agrobacterium tumefaciens* mediated genetic transformation.
(4) Since the caffeine fraction of tea leaf with virulence activity is obtained without involving any expensive instruments or costly extraction methods, its use proves to be an economical method.
(5) The caffeine fraction of tea leaf with virulence inducing ability can be easily obtained in abundance from naturally growing tea bushes round the year.
(6) The caffeine fraction of tea leaf with virulence inducing ability is of natural origin and is not of synthetic or semi-synthetic nature.
(7) The caffeine fraction of tea leaf with virulence inducing ability can be obtained in abundance from even the lower maintenance foliage thereby, making it more economical as generally such leaves are discarded or burnt.
(8) The caffeine fraction of tea leaf can also be used as an agent with virulence inducing ability in different in vitro systems involving different plants or explants.
(9) The caffeine fraction of tea leaf with virulence inducing ability can also be used during 'hairy root production' using *Agrobacterium rhizogenesis*.
(10) The caffeine fraction of tea leaf with virulence inducing ability can be used to increase the efficiency of *Agrobacterium* mediated transformation.

The invention claimed is:

1. A thermolabile caffeine fraction produced by a method comprising:
   a. extracting dried tea leaves with about 10-40 weight % aqueous acetone to obtain an aqueous acetone fraction,
   b. extracting the aqueous acetone fraction of step (a) with n-hexane to obtain an aqueous layer and a lipid layer,
   c. extracting the aqueous layer with petroleum ether and ethyl acetate to remove catechins from the aqueous layer, and
   d. extracting the aqueous layer resulting from of step (c) with chloroform to obtain a chloroform fraction containing caffeine.

2. The thermolabile caffeine fraction of claim 1, wherein the method further comprises concentrating the chloroform fraction to a lesser volume.

* * * * *